United States Patent [19]

Jones

[11] Patent Number: 5,527,956
[45] Date of Patent: Jun. 18, 1996

[54] PROCESS FOR THE OXIDATION OF AROMATIC METHYL GROUPS

[75] Inventor: Richard G. Jones, Westhoughton, United Kingdom

[73] Assignee: Solvay Interox Limited, Warrington, England

[21] Appl. No.: 356,260

[22] PCT Filed: May 27, 1993

[86] PCT No.: PCT/GB93/01112

§ 371 Date: Dec. 15, 1994

§ 102(e) Date: Dec. 15, 1994

[87] PCT Pub. No.: WO94/00407

PCT Pub. Date: Jan. 6, 1994

[30] Foreign Application Priority Data

Jun. 24, 1992 [GB] United Kingdom ............... 9213420

[51] Int. Cl.$^6$ .................................................. C07C 51/16
[52] U.S. Cl. ............................................. 562/409; 562/456
[58] Field of Search ........................... 562/456, 409

[56] References Cited

U.S. PATENT DOCUMENTS

| 4,923,580 | 5/1990 | Turner et al. | 204/157.97 |
| 5,092,971 | 3/1992 | Turner et al. | 204/157.99 |

*Primary Examiner*—José G. Dees
*Assistant Examiner*—Samuel Barts
*Attorney, Agent, or Firm*—Larson and Taylor

[57] ABSTRACT

Fluro-substituted aromatic carboxylic acids, and particular 2- and 4-fluorobenzoic acid can be made from the corresponding fluoro-methyl compound such as fluorotoluene in a single stage by the reaction at elevated temperature, preferably of at least 80° C. with hydrogen peroxide and bromide in mole ratios to the substrate of greater than 2:1, and preferably around 3:1, in the presence of means capable of generating bromine free radicals from bromine molecules, such as radiation having a wavelength of not greater than 600 nm or an organic peroxide.

17 Claims, No Drawings

PROCESS FOR THE OXIDATION OF AROMATIC METHYL GROUPS

This application was filed under U.S.C. of the application Ser. No. PCT/GB93/01112 filed May 27, 1993.

The present invention relates to a process for the production of aromatic carboxylic acids and more particularly fluoro-substituted aromatic carboxylic acids.

Fluoro substituted aromatic carboxylic acids are intermediates in the manufacture of pharmaceuticals and/or agrochemicals. A number of processes for their production employ an alkyl substituted fluoroaromatic compound as starting material but these can require specialist equipment such as electrochemical cells, or elevated pressure or specialist techniques as in enzymatic oxidation.

In European Patent Application numbers EP-A-0 336 567 and EP-A-0 336 568 there are disclosed processes for selectively monobrominating or dibrominating an alkyl side chain of an aromatic compound substituted by an electron withdrawing group, viz o-nitrotoluene with aqueous hydrogen peroxide and a source of bromine under photolytic conditions. In accordance with accepted understanding of aromatic substitution reactions, the electron-withdrawing substituent on the benzene nucleus tended to deactivate the substrate, thereby inhibiting its ability to participate in substitution reactions. Although the reaction mixture included a significant aqueous phase, further reaction of the brominated products for example by hydrolysis was substantially avoided. Thus, the brominated products were available for further processing, for example to the eventual production of o-nitrobenzoic acid, but an overall conversion from alkyl to carboxylic acid required the addition of further and potentially cumbersome processing stages which inevitably introduces additional processing costs and reduces throughput in apparatus of a given size.

Surprisingly, it has been found that in a related class of alkylaromatic compounds nuclearly substituted by an electron withdrawing group, the alkyl group can be converted in a single stage to a carboxylic acid group, rather than requiring a series of stages.

According to the present invention there is provided a process for the conversion of a methyl substituent of an aromatic compound in which the aromatic compound is brought into contact with hydrogen peroxide and aqueous hydrogen bromide solution in the presence of means for generating bromine radicals from bromine molecules characterized in that the aromatic compound is nuclearly substituted by a fluoro group, the contact is effected at an elevated reaction temperature and hydrogen peroxide and aqueous hydrogen bromide solution are each employed in a mole ratio to the fluoro-substituted aromatic compound of greater than 2:1, whereby the methyl substituent is converted to a carboxylic acid substituent.

By the use of a process according to the present invention, the conversion of methyl to carboxylic acid substituent can be carried out in a single stage, despite the presence of a deactivating substituent.

The process of the present invention is particularly suited to the conversion of fluorotoluenes to fluorobenzoic acid, i.e. compounds meeting the general formula i to ii:

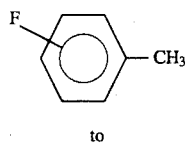

to

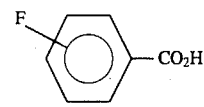

Especially suitably, the fluoro substituent is ortho or para to the methyl substituent.

In general, hydrogen bromide is employed in a concentrated solution, advantageously greater than 15% w/w and in many practical instances greater than about 30% w/w. In general, bromide is present in a mole ratio to the fluorotoluene of from about 2.5:1 to about 7.5:1, and in some selected embodiments at from about 2.5:2 to about 3.5:1. It can be introduced as such or be obtained by in situ acidification of a soluble bromide salt, such as an alkali metal salt, or by in situ reduction of bromine. During the course of the reactions which take place in the single stage, bromide is oxidised to bromine which, it is believed, in a free-radical based reaction, brominates the methyl substituent of the fluorotoluene. The brominated substituent is subsequently hydrolysed or perhydrolysed, releasing bromide and oxidised through to the carboxylic acid, possibly via a further molar equivalent of bromine generated in situ from hydrogen peroxide and bromide.

It is preferable to employ greater than 2.5 moles hydrogen peroxide per mole of fluorotoluene and in practice the amount is often selected in the range of from about 2.7 to 4 moles per mole of fluorotoluene. A higher mole ratio than 4:1 such as up to 6:1 can be employed, but is less cost effective. The hydrogen peroxide solution is preferably introduced into the reaction mixture in the form of a concentrated solution, which advantageously is at least 35% w/w, is normally not greater than about 85% w/w and in many instances is selected in the range of 35% up to 75% w/w. The use of concentrated hydrogen peroxide solutions introduces less diluent water into the reaction mixture, and accordingly means that during subsequent reuse of the aqueous medium, less processing or additional bromide will be needed to maintain the concentration of bromide at an acceptable level, for example to restore its concentration to that pertaining during the first reaction.

It is preferable to introduce the hydrogen peroxide progressively during the course of all or a substantial fraction of the reaction period, rather than introduce all of the peroxide at the start of the reaction. Progressive introduction includes its introduction continuously or in a plurality of fractions. By so doing, it is possible to employ the hydrogen peroxide more efficiently for the desired conversion of methyl to carboxylic acid. In addition, the progressive introduction of peroxide tends towards minimising the concentration of peroxide at any chosen instant during the reaction and thereby enhance safety of operation.

In an important aspect of the present .invention, free radicals are generated in the reaction mixture during the period in which the substrate is being brominated at its methyl-substituent. The invention contemplates two methods for their generation, one comprising the irradiation of the reaction mixture with light of at least the minimum frequency to dissociate bromine molecules to bromine free radicals and the second comprising the introduction of chemical free radical generator, such as particularly an organic peroxide which can dissociate at the selected reaction temperature.

Effective light has a wavelength of not greater than about 600 nm and in practice it can be provided conveniently from commercially available lamps having principal emissions in the range of 250 nm to 600 nm, often described as daylight emission lamps such as high pressure sodium discharge lamps, mercury fluorescent lamps or tungsten or tungsten halogen lamps. The arrangement of such lamps relative to the reaction mixture is at the discretion of the process operator. For example, they can be positioned within or above the mixture or can shine through transparent wall or floor sections. As a general rule, there is a relationship between the intensity of the radiation and rate at which at least the bromination reactions occur. It is often desirable to select an illuminance of at least $10^4$ lux and in many instances at least $10^5$ lux. Illuminance is rarely above $10^8$ lux.

Suitable peroxides which may be employed as generators of radicals include benzoyl peroxide, methylethyl ketoperoxide, t-butylperpivalate, diisopropylperoxydicarbonate and t-butylhydroperoxide. Suitable non-peroxide radical generators include azobisisobutyronitrile. Preferably, they are introduced progressively during the period of introduction of the hydrogen peroxide. They are conveniently employed in a catalytic amount usually of less than about 0.1 mole per mole of fluorotoluene such as a mole ratio of from about 1:100 to about 1:1000.

The reaction is often conducted at a temperature of greater than 60° C., and at above 80° C. at least during the period when hydrogen peroxide is present in the reaction mixture. In especially preferred embodiments, the reaction is conducted at or within 10° C. of the reflux temperature of the mixture, i.e. at or in excess of 100° C.

The reaction period is usually selected in the range of from about 1 to 10 hours, measured from the start of the introduction of the hydrogen peroxide. Typically, the hydrogen peroxide is introduced during the initial fraction of from about 1 to about 6 hours and often comprises about 40% to about 90% or more of the overall reaction period.

At the end of the reaction period, the carboxylic acid product tends to precipitate out of solution and the solid material can be recovered by conventional passive or active solid/liquid separating techniques, including settling/decantation, centrifugation and filtration techniques. Solids recovery can be enhanced by cooling the reaction mixture to ambient temperature or lower, for example to 10° C. or lower.

The separated aqueous liquid phase contains not only recoverable and re-usable bromide, but additionally comprises a saturated solution of carboxylic acid product. Advantageously, if the phase is employed as the medium for a subsequent reaction with a further amount of fluorotoluene as substrate, often after removal of the volume of hydrogen peroxide solution introduced during the reaction process, the bromide is reused and losses of product in the aqueous phase are minimised since the medium already contains sufficient product to saturate it at the cooled temperature of 5° to 10° C.

Having described the invention in general terms, specific embodiments thereof will now be provided in greater detail by way of example only.

EXAMPLE 1

A glass flask, 250 ml, mounted on a heater and fitted with a thermocouple, condenser, liquid inlet port and a mechanical stirrer was charged with 4-fluorotoluene, 11.0 g (0.1 mol) and a solution of hydrobromic acid in water, 50.62 g of a 48% w/w solution, providing 0.3 mol $Br^{13}$. The flask was irradiated by a 500 w quartz halogen lamp placed 3 cm from the flask wall, providing mainly light in the visible range. The reaction mixture was warmed gradually to 60° C., whereupon introduction of an aqueous hydrogen peroxide solution, 14.55 g, 70% w/w providing 0.3 mol, commenced and continued for the next 100 minutes. The reaction during that period was maintained near the temperature range of 80° to 100° C. The reaction was permitted to continue for a further hour after all the hydrogen peroxide had been introduced, so that the total reaction period was 2 hours 40 minutes. The mixture was then cooled rapidly to between 5° and 10° C. with formation of a solid precipitate which was removed by filtration, water washed and dried in a vacuum desiccator. The solid product and filtered liquor were both analysed by conventional gas liquid chromatography to determine their content of 4-fluorobenzoic acid.

EXAMPLE 2

The procedure of Example 1 was repeated, but employing a 3 hour addition time for the hydrogen peroxide with irradiation continuing for a further 20 minutes giving a total reaction time of 3 hours 20 minutes.

EXAMPLE 3

The procedure of Example 1 was repeated, but with addition of hydrogen peroxide commencing at 55° C., continuing for 90 minutes, with irradiation over a further 55 minutes giving a total reaction time of 2 hours 25 minutes.

EXAMPLE 4

The procedure of Example 3 was repeated, but the irradiating lamp was a 200 watt lamp placed 3 cm from the flask, with addition of hydrogen peroxide commencing at 58° C. continuing for 55 minutes, with irradiation over a further 25 minutes giving a total reaction time of 1 hour 20 minutes.

EXAMPLE 5

The procedure of Example 1 was repeated, except that a double quantity of hydrobromic acid solution, 0.6 mol was employed and the hydrogen peroxide solution was added over 40 minutes.

EXAMPLE 6

The process of Example 1 was repeated, except that no lamp was employed, the source of illumination comprising ambient sunlight on a sunny day in England, addition of hydrogen peroxide commenced at a temperature of 97° C. and the hydrogen peroxide was added over 55 minutes, giving a total reaction time of 1 hour 55 minutes.

EXAMPLE 7

The procedure of Example 1 was repeated, except that the flask was not irradiated, the hydrogen peroxide was added over 50 minutes, the reaction was maintained at reflux (96° to 100° C.) for a further 50 minutes giving a total reaction time of 1 hour 40 minutes and a total of 1.06 g benzoyl peroxide (0.003 mole) was added in aliquots at regular intervals throughout the addition of hydrogen peroxide.

EXAMPLE 8

The process of Example 1 was repeated, except that 2-fluorotoluene was employed as substrate, 0.2 mol (9.7 g) of hydrogen peroxide was added over 35 minutes, followed by 90 minutes of further irradiation, then 0.1 mol (4.85 g) of hydrogen peroxide was added over 15 minutes and reaction continued for a further hour giving a reaction time of 3 hours 20 minutes.

Comparison A

In Comparison A, the procedure of Example 1 was repeated, except that the reaction was conducted in a darkened vessel excluding all light, hydrogen peroxide addition commenced when the temperature was 71° C. for a period of 85 minutes and the reaction was continued for a further 35 minutes giving a total reaction time of 2 hours.

Comparison B

The process of Example 3 was repeated, except that air was passed through the reaction mixture throughout the reaction, only 0.2 mol of hydrogen peroxide and hydrogen bromide, i.e. respectively 9.7 g peroxide solution and 37.33 g bromide solution were employed and the reaction continued for 45 minutes after the addition of hydrogen peroxide finished giving a reaction time of 1 hour 40 minutes.

Comparison C

The process of Example 1 was repeated, except that 4-t-butyltoluene (14.82 g, 0.1 mole) was employed as the substrate, addition of hydrogen peroxide commenced at 62° C., the addition time was 1 hour 10 minutes and reaction was continued for a further 20 minutes giving a total reaction time of 1 hour 30 minutes.

Comparison D

The process of Example 1 was repeated, except that 4-chlorotoluene (12.6 g, 0.1 mole) was employed as the substrate, addition of hydrogen peroxide commenced at 53° C., the addition time was 1 hour 30 minutes and reaction was continued for a further 60 minutes giving a total reaction time of 2 hours 30 minutes.

Comparison E

The process of Example 1 was repeated, except that 4-bromotoluene (17.21 g, 0.1 mole) was employed as the substrate, addition of hydrogen peroxide commenced at 78° C., the addition time was 1 hour 10 minutes and reaction was continued for a further 60 minutes giving a total reaction time of 2 hours 10 minutes.

The yields of carboxylic acid product are summarised in the Table below. Analysis confirmed that in all the Examples and Comparisons, all the substrate had been converted. The figure quoted in the Table for the yield expressed as a % of substrate is the sum of the carboxylic acid precipitated as a solid or remaining in the liquor. ND indicates that none was detectable

TABLE

| Example/ Comparison | Yield of carboxylic acid | | |
|---|---|---|---|
| | Solid wt g | Liquor wt g | % of substrate |
| Ex1 | 6.42 | 5.2 | 96 |
| Ex2 | 12.32 | ND | 88 |
| Ex3 | 11.77 | ND | 84 |
| Ex4 | 10.42 | ND | 75 |
| Ex5 | 9.97 | ND | 71 |
| Ex6 | 7.86 | 1.34 | 66 |
| Ex7 | 10.23 | 1.86 | 86 |
| Ex8 | 12.31 | trace | 88 |
| Comp A | 5.05 | ND | 36 |

TABLE-continued

| Example/ Comparison | Yield of carboxylic acid | | |
|---|---|---|---|
| | Solid wt g | Liquor wt g | % of substrate |
| Comp B | 1.79 | 0.83 | 19 |
| Comp C | 1.80 | 0.36 | 12 |
| Comp D | 4.80 | <0.1 | 31 |
| Comp E | 4.90 | <0.1 | 24 |

By comparing the yields obtained in Examples 1 to 3 with that obtained in Comparison A, it can be seen that a much greater conversion of substrate to carboxylic acid product is obtained when the reaction mixture is illuminated with visible light. Comparison of Example 2 with Example 4 and Example 5 demonstrates that the light intensity affects the yield of product obtained. Example 7 demonstrates that a significant extent of carboxylic acid production can be obtained by employing an organic peroxide instead of illumination to generate free radicals during the course of the reaction. Comparison B demonstrates that if insufficient reagent is present, the reaction does not progress to a significant extent to the desired carboxylic acid. Comparisons C, D and E demonstrate that conversion to the carboxylic acid occurs to a much lesser extent under otherwise identical process conditions when the substrate contains related substituents such as chloro, bromo or t-butyl instead of fluoro.

I claim:

1. A process for the conversion of a methyl substituent of an aromatic compound substrate in which the aromatic compound is brought into contact with hydrogen peroxide and aqueous hydrogen bromide solution in the presence of means for generating bromine radicals from bromine molecules characterized in that the aromatic compound is nuclearly substituted by a fluoro group, the contact is effected at an elevated reaction temperature, and hydrogen peroxide and aqueous hydrogen bromide solution are each employed in a mole ratio to the fluoro-substituted aromatic compound of greater than 2:1, whereby the methyl substituent is converted to a carboxylic acid substituent.

2. A process according to claim 1 characterized in that the fluoro-substituted aromatic compounds is represented by general formula:

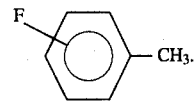

3. A process according to claim 1 or 2, characterized in that the fluoro-substituent is ortho or para to the methyl substituent.

4. A process according to claim 1 or 2, characterized in that hydrogen peroxide is employed in a mole ratio to the substrate of from 2.7:1 to 4:1.

5. A process according to claim 1 or 2, characterized in that the hydrogen bromide is present in a mole ratio to the substrate of 2.5:1 to 3.5:1.

6. A process for the conversion of ortho or para fluorotoluene in which the ortho or para fluorotoluene is brought into contact with hydrogen peroxide and aqueous hydrogen bromide solution at an elevated reaction temperature in the presence of means for generating bromine radicals from bromine molecules, the hydrogen peroxide being employed in a mole ratio to fluorotoluene of from 2.7:1 to 4:1, the aqueous hydrogen bromide solution being employed in a mole ratio to fluorotoluene of from 2.5:1 to 3.5:1, whereby the ortho or para fluorotoluene is converted to ortho or para fluorobenzoic acid.

7. A process according to claim 1, 2 or 6, characterized in that the hydrogen peroxide is employed at a concentration of from 35% w/w to 75% w/w.

8. A process according to claim 1, 2 or 6, characterized in that the concentration of bromide in the aqueous phase is at least 30% w/w.

9. A process according to claim 1, 1 or 6, characterized in that the means for generating radicals comprises radiation having a wavelength not greater than 600 nm.

10. A process according to claim 1, 2 or 6, characterized in that means for generating radicals comprises a catalytic amount of an organic peroxide.

11. A process according to claim 1, 2 or 6, characterized in that the hydrogen peroxide is introduced progressively into the reaction mixture during 40 to about 90% of the reaction period.

12. A process according to claim 1, 2 or 6, characterized in that the reaction period is from 1 to 10 hours.

13. A process according to claim 1, 2 or 6, characterized in that the reaction is conducted at a temperature of from 80° C. up to the reflux temperature of the aqueous phase.

14. A process according to claim 1, 2 or 6, characterized in that the reaction mixture is cooled or allowed to cool to a temperature of below 10° C. and the resultant solid precipitate is separated from its supernatant liquor and retained as product.

15. A process according to claim 1, 2 or 6, in which the organic phase is essentially free of organic solvent.

16. A process according to claim 1, 2 or 6, in which the reaction temperature is maintained at above 80° C. at least when hydrogen peroxide is present in the reaction mixture.

17. A process according to claim 1, 2 or 6, in which the reaction temperature is maintained at least at 100° C.

* * * * *